United States Patent [19]

Bair

[11] Patent Number: 4,810,727

[45] Date of Patent: Mar. 7, 1989

[54] CHRYSENE COMPOUND

[75] Inventor: Kenneth W. Bair, Chapel Hill, N.C.

[73] Assignee: Burroughs Wellcome Co., Research Triangle Park, N.C.

[21] Appl. No.: 83,238

[22] Filed: Aug. 6, 1987

Related U.S. Application Data

[60] Division of Ser. No. 663,039, Oct. 18, 1984, Pat. No. 4,719,048, which is a continuation-in-part of Ser. No. 495,512, May 17, 1983, abandoned.

[51] Int. Cl.$^4$ .................... A61K 31/135; C07C 93/00
[52] U.S. Cl. ................ 514/655; 260/501.18; 260/501.21; 564/387; 564/426
[58] Field of Search ............. 560/38, 39; 564/426, 564/387; 514/727, 654, 908, 655; 260/501.18, 501.21

[56] References Cited

U.S. PATENT DOCUMENTS

| | | | |
|---|---|---|---|
| 2,530,065 | 11/1950 | King | 560/39 |
| 2,547,150 | 11/1951 | Kerwin et al. | 260/501.18 |
| 3,198,802 | 8/1965 | Clark et al. | 560/38 |
| 4,511,582 | 4/1985 | Bair | 514/654 |
| 4,530,800 | 7/1985 | Bair | 260/501.21 |
| 4,532,344 | 7/1985 | Bair | 260/252 |
| 4,551,282 | 7/1985 | Bair | 260/501.18 |
| 4,719,046 | 1/1988 | Bair | 260/501.18 |
| 4,719,047 | 1/1988 | Bair | 260/501.18 |
| 4,719,048 | 1/1988 | Bair | 260/501.18 |
| 4,719,049 | 1/1988 | Bair | 260/501.18 |
| 4,719,055 | 1/1988 | Bair | 260/501.12 |
| 4,719,236 | 1/1988 | Bair | 514/577 |
| 4,720,587 | 1/1988 | Bair | 564/387 |

FOREIGN PATENT DOCUMENTS 743137 9/1966 Canada .................. 564/426

OTHER PUBLICATIONS

Hrabowska, M. et al., "Antitumor Activity of 1-Nitro-9-amminoacridine Periative", Argneium-Forsch./Drug Kes., 32(11), No. 9, (1987), 1013–1016.

Primary Examiner—Glennon H. Hollrah
Assistant Examiner—Raymond Covington
Attorney, Agent, or Firm—Donald Brown

[57] ABSTRACT

The present invention relates to compounds of formula (I)

$$ArCH_2R^1 \qquad (I)$$

or a monomethyl or a monoethyl ether thereof (the compound of formula (I) including these ethers may contain no more than 30 carbon atoms in total); ethers, esters thereof; acid addition salts thereof; wherein Ar is a chrysene or substituted chrysene ring system; $R^1$ contains not more than eight carbon atoms and is a group

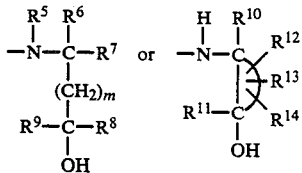

wherein m is 0 or 1;
$R^5$ is hydrogen;
$R^6$ and $R^7$ are the same or different and each is hydrogen or $C_{1-3}$ alkyl optionally substituted by hydroxy;
$R^8$ and $R^9$ are the same or different and each is hydrogen or $C_{1-3}$ alkyl;
—C—C— is a five- or six-membered saturated carbocyclic ring;
$R^{10}$ is hydrogen, methyl or hydroxymethyl;
$R^{11}$, $R^{12}$ and $R^{13}$ are the same or different and each is hydrogen or methyl;
$R^{14}$ is hydrogen, methyl, hydroxy, or hydroxymethyl.

7 Claims, No Drawings

CHRYSENE COMPOUND

This is a division of co-pending application Ser. No. 663,039, filed on Oct. 18, 1984, now U.S. Pat. No. 4,719,048, which is a continuation-in-part of Ser. No. 495,512, filed May 17, 1983, now abandoned.

The present invention relates to polycyclic aromatic alkanol derivatives which have been found to have biocidal activity. More specifically the invention concerns aminoalkanol derivatives containing a polycarbocyclic aromatic ring system, methods for the synthesis thereof, pharmaceutical formulations thereof, novel intermediates therefor, pharmaceutical formulations thereof and the use thereof as biocidal agents, particularly antitumor agents.

Accordingly, in a first aspect, the present invention provides a compound of the formula (I)

$$ArCH_2R^1 \qquad (I)$$

or a monomethyl or monoethyl ether thereof (the compound of formula (I) including these ethers may contain no more than 30 carbon atoms in total); ethers, esters thereof; acid addition salts thereof;
wherein
Ar is a chrysene ring optionally substituted by one or two substituents (the substituents will contain not more than four carbon atoms in total when taken together being the same or different and are selected from halogen; cyano; $C_{1-4}$ alkyl or $C_{1-4}$ alkoxy, each optionally substituted by hydroxy or $C_{1-2}$ alkoxy; halogen substituted $C_{1-2}$ alkyl or $C_{1-2}$ alkoxy; a group $S(O)_nR^2$ wherein n is an integer 0, 1 or 2 and $R^2$ is $C_{1-2}$ alkyl optionally substituted by hydroxy or $C_{1-2}$ alkoxy; or the chrysene ring is optionally substituted by a group $NR^3R^4$ containing not more than 5 carbon atoms wherein $R^3$ and $R^4$ are the same or different and each is a $C_{1-3}$ alkyl group or $NR^3R^4$ forms a five- or six-membered heterocyclic ring optionally containing one or two additional heteroatoms);
$R^1$ contains not more than eight carbon atoms and is a group

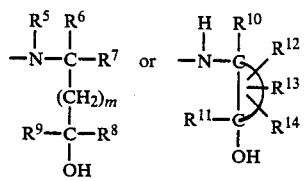

wherein m is 0 or 1;
$R^5$ is hydrogen;
$R^6$ and $R^7$ are the same or different and each is hydrogen or $C_{1-3}$ alkyl optionally substituted by hydroxy;
$R^8$ and $R^9$ are the same or different and each is hydrogen or $C_{1-3}$ alkyl;
—C—C— is a five- or six-membered saturated carbocyclic ring;
$R^{10}$ is hydrogen, methyl or hydroxymethyl;
$R^{11}$, $R^{12}$ and $R^{13}$ are the same or different and each is hydrogen or methyl;
$R^{14}$ is hydrogen, methyl, hydroxy, or hydroxymethyl.

Suitably $ArCH_2R^1$ or a monomethyl or monethyl ether thereof contains not more than 28 carbon atoms in total.

Ar is suitably 6-chrysenyl,

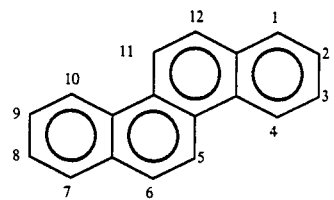

suitably m is 0, suitably $R^1$ is

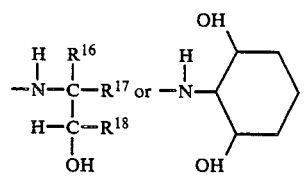

wherein
$R^{16}$ is $CH_2OH$, $CH(CH_3)OH$ or $CH_2CH_2OH$,
$R^{17}$ is hydrogen, $C_{1-3}$ alkyl or $CH_2OH$,
$R^{18}$ is hydrogen or methyl.
Preferably $R^{16}$ is $CH_2OH$ or $CH(CH_3)OH$; $R^{17}$ is hydrogen, methyl, ethyl or $CH_2OH$.
Most preferably $R^1$ is a diol of the structure

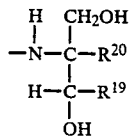

wherein $R^{19}$ is hydrogen or methyl and $R^{20}$ is hydrogen, methyl or ethyl, preferably methyl.

Acid addition salts included within the scope of the present invention are those of compound of formula (I) and ethers and esters thereof.

Esters and nonpharmaceutically useful acid addition salts of the compounds of the formula (I) are useful intermediates in the preparation and purification of compounds of the formula (I) and pharmaceutically useful acid addition salts thereof, and are therefore within the scope of the present invention. Thus, acid addition salts of the compounds of the formula (I) useful in the present invention include but are not limited to those derived from inorganic acids, such as hydrochloric, hydrobromic, sulfuric and phosphoric acids, and organic acids such as isethionic (2-hydroxyethylsulfonic), maleic, malonic, succinic, salicylic, tartaric, lactic, citric, formic, lactobionic, pantothenic, methanesulfonic, ethanesulfonic, benzenesulfonic, p-toluenesulfonic, naphthalene-2-sulfonic, and ascorbic acids, and amino acids such as glycine.

Acid addition salts particularly useful as biocidal agents are those that are pharmacologically and pharmaceutically acceptable. Thus, suitable acid addition salts include but are not limited to those derived from hydrochloric, methanesulfonic, ethanesulfonic, isethionic, lactic, and citric acids.

The preferred pharmacologically and pharmaceutically acceptable acid addition salts are those that are soluble in solvents suitable for parenteral administration, for example, hydrochlorides, methanesulfonates and isethionates.

Esters of compounds of formula (I) are derived from acids known to those skilled in the art to be suitable for ester formation, and are conveniently those derived from $C_{1-6}$ alkanoic acids or alkanoic acid derivatives, for example acetic acid, propionic acid, n-butyric acid and iso-butyric acid. The esters may be formed from all or only some of the hydroxy groups contained in the compounds of formula (I). Specific compounds within the scope of formula (I) include;
2-((6-Chrysenylmethyl)amino)-2-methyl-1-propanol,
2-((3-Chrysenylmethyl)amino)-2-methyl-1,3-propanediol,
2-((2-Chrysenylmethyl)amino)-2-methyl-1,3-propanediol,
2-((6-Chrysenylmethyl)amino)-2-methyl-1,3-propanediol,
2-((6-Chrysenylmethyl)amino)-2-hydroxymethyl-1,3-propanediol,
2-((6-Chrysenylmethyl)amino)-2-ethyl-1,3-propanediol,
(+ —)  (2R*,3R*)-2-((6-Chrysenylmethyl)amino)-2-methyl-1,3-butanediol,
(+ —)  (2R*,3S*)-2-((6-Chrysenylmethyl)amino)-2-methyl-1,3-butanediol,
2-((6-Chrysenylmethyl)amino)-2-ethoxymethyl-1,3-propanediol,
3-Methoxy-2-((6-chrysenylmethyl)amino)-2-methyl-1-propanol,
($1\alpha,2\beta,3\alpha$)-2-((6-Chrysenylmethyl)amino)-1,3-cyclohexanediol,
2-((6-Chrysenylmethyl)amino)-2-isopropyl-1,3-propanediol,
2-((6-Chrysenylmethyl)amino)-2-methyl-1,4-butanediol,
(+ —) (2R*,3RS*,4R*)-3-(6-Chrysenylmethyl)amino)-3-methyl-2,5-pentanediol,
meso-3-((6-Chrysenylmethyl)amino)-2,4-pentanediol,
2-((6-Chrysenylmethyl)amino)-1,3-propanediol,
2-(((12-Ethyl-6-chrysenyl)methyl)amino)-2-methyl-1,3-propanediol,
2-(((12-Chloro-6-chrysenyl)methyl)amino)-2-methyl-1,3-propanediol and
2-(((12-Ethoxy-6-chrysenyl)methyl)amino)-2-methyl-1,3-propanediol;
ethers, esters thereof; acid addition salts thereof.

Of these specific examples of compounds of formula (I), the preferred compounds are 2-((6-chrysenylmethyl)amino)-2-methyl-1,3-propanediol, (+ —) (2R*,3R*)-2-((6-chrysenylmethyl)amino)-2-methyl-1,3-butanediol, and (+ —) (2R*,3S*)-2-((6-chrysenylmethyl)amino)-2-methyl-1,3-butanediol; ethers, esters thereof; acid addition salts thereof.

Of these specific examples of comppounds of formula (I), the most preferred compounds is 2-((6-chrysenylmethyl)amino)-2-methyl-1,3-propanediol; ethers, esters thereof; acid addition salts thereof.

The compounds of formula (I) and their ethers, esters and salts thereof may be prepared by any method known in the art for the preparation of compounds of analogous structure. Thus, the compounds of formula (I) may, for example, be prepared by any of the methods defined below.

1. The reduction of a compound of formula (II)

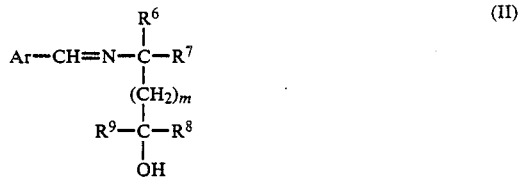

Wherein $R^1$-$R^4$ are as hereinbefore defined or an appropriately protected derivative thereof followed by deprotection where appropriate.

The conditions and reagents for such a reaction are well known to those skilled in the art, and any such conditions/reagents may be employed. The conversion of (II) or suitably protected derivatives thereof may be carried out by a reducing agent followed by deprotection if necessary. The reduction is conveniently carried out by a metal hydride such as lithium aluminum hydride, sodium borohyride, sodium cyanoborohydride, or by catalytic hydrogenation, conveniently by hydrogen in the presence of a metal catalyst such as palladium or platinum, or equivalent reagents as outlined by J. March, *Advanced Organic Chemistry*, 2nd ed., pages 819–820, McGraw Hill, New York, 1977. The reduction is suitably carried out with the compound of formula (II) in solution in an inert solvent or mixture of solvents compatible with the reducing agent, at a non-extreme temperature, for example, between 0° and 80° C., conveniently at room temperature.

In the case of lithium aluminum hydride and like reagents, suitable solvents include ethers (for example tetrahydrofuran, diethyl ether and 1,2-dimethoxyethane) optionally in the presence of a hydrocarbon cosolvent (for example toluene, benzene or hexane).

In the case of sodium borohydride and like reagents, suitable solvents include alcohols (for example ethanol, methanol or isopropanol) optionally in the presence of a hydrocarbon cosolvent (for example toluene, benzene or hexane) or an ether cosolvent (for example diethylether or tetrahydrofuran).

In the case of sodium cyanoborohydride and like reagents, suitable solvents include those described for sodium borohydride and in the presence of an acid conveniently glacial acetic acid or ethanolic hydrochloric acid as outlined in, for example, R. Hutchins et al., *Organic Preparations and Procedures International* 11. 201 (1979).

In the case of catalytic hydrogenation, suitable solvents include alcohols (for example methanol and ethanol) optionally in the presence of a hydrocarbon cosolvent (for example toluene or benzene) or ether cosolvent (for example diethyl ether or tetrahydrofuran) in the presence of an acid (for example glacial acetic acid or ethanolic hydrochloric acid) or in glacial acetic acid.

Protected derivatives of compounds of formula (II) are conveniently used when lithium aluminum hydride is employed as the reducing agent. Convenient protecting groups are compatible with the reducing agent utilized and are readily removed under nondestructive conditions, for example benzyl, tetrahydropyranyl and isopropylidene ethers.

It is often convenient not to isolate the compound of the formula (II) but to react a compound of the formula (III) with a compound of the formula (IV):

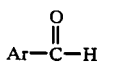

(III)

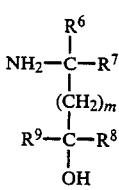

(IV)

wherein Ar and $R^1$-$R^4$ are as defined in (I), and reduce the compound of the formula (II) so formed in situ. The reaction of the compounds of the formulae (III) and (IV) is again suitably carried out using conditions and reagents which are well known to those skilled in the art, for example in the presence of an acid, such as a sulfonic acid, i.e. p-toluenesulfonic acid, in an appropriate inert solvent, such as an aromatic hydrocarbon, suitably toluene, with azeotropic removal of water followed by treatment with the reducing agent in an appropriate solvent, suitably ethanol or methanol. Alternatively, (II) formed under equilibrium conditions in appropriate solvents can be reduced in situ with an appropriate reducing agent, suitably sodium cyanoborohydride. The compound of formula (III) may be in the form of a protected aldehyde, for example an acetal, which liberates the aldehyde function under the reaction conditions.

In turn, a compound of formula (III) can be synthesized by reacting the appropriate polycyclic aromatic hydrocarbon with a formylating agent such as that generated by the reaction between $SnCl_4$ and $Cl_2CHOCH_3$ or equivalent reagents, for example, according to the method of A. Reiche et al., *Chem. Ber.* 93, 88 (1960), or with other standard formylating reagents/procedures known to the art, for example, the Gatterman-Koch reaction (CO/HCl/$AlCl_3$/CuCl), the Gatterman reaction (HCN/HCl/$ZnCl_2$), and the Vilsmeier reaction ($POCl_3$/PhN(Me)CHO, or $POCl_3$/$Me_2NCHO$) (J. March, vide supra, pages 494–497).

The compounds of the formula (III) may also be prepared from an appropriate polycyclic aromatic hydrocarbon substituted by a suitable functional group such as $CH_2OH$, $CHBr_2$, $CH_3$, $COCH_3$, COOH, or CN, and converting this functional group to an aldehyde group by methods well known to those skilled in the art.

Where the polycyclic aromatic ring bears substituents, the compound of formula (III) may be prepared by a variety of methods known in the art of organic chemistry depending on the nature of the substituent on the polycyclic ring. For example, if the substituent(s) is a halogen, the starting materials may be prepared by direct treatment of the polycyclic aromatic hydrocarbon with a halogenating agent (e.g. $Cl_2$, $Br_2$, or $SO_2Cl_2$) or indirectly by such routes as the Sandmeyer reaction (H. H. Hodgson, *Chem. Rev.* 40, 251 (1947). If the substituent(s) is alkyl, the polycyclic aromatic hydrocarbon may be reacted with the appropriate reagents under Friedel-Crafts reaction conditions (G. A. Olah, *Friedel Crafts and Related Reactions*, Vols. 1-3, Interscience, New York, NY, 1963-1965).

The compounds of the formula (IV) also may be prepared by methods known in the art, for example, by the reaction of compound $NO_2CH_2R^2$ with an appropriate aldehyde, conveniently acetaldehyde or formaldehyde (as in B. M. Vanderbilt and H. B. Hass, *Ind. Eng. Chem.* 32, 34 (1940)) followed by reduction (as outlined in J. March, vide supra, pages 1125–1126), conveniently by hydrogen and a metal catalyst (for example, a platinum containing catalyst) in an appropriate solvent, conveniently glacial acetic acid.

2. The reduction of a compound of the formula (V)

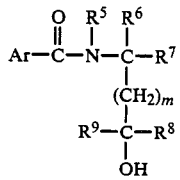

(V)

wherein Ar and $R^1$-$R^4$ are as hereinbefore defined and the hydroxy groups are optionally protected, followed by deprotection of the hydroxy groups where appropriate. The reduction may be carried out by standard reducing agents known for carrying out this type of reduction (as outlined in J. March, vide supra page 1122), for example, a hydride reagent such as lithium aluminium hydride in an inert solvent, such as an ether, i.e. tetrahydrofuran, at a non-extreme temperature, for example, at between 0° and 100° C. and conveniently at the reflux temperature of the ether. The compound of the formula (V) may be formed by the reaction of the appropriate acid (ArCOOH) or a suitable reactive acid derivative thereof (as outlined in J. March, vide supra, pages 382–390), for example, an acid halide, in an inert solvent with an amine of the formula (IV) in which the hydroxy groups are optionally protected, for example, when the compound of the formula (IV) is a diol, by an isopropylidene group. The compound of the formula (V) so formed is suitably reduced in situ and deprotected if necessary to give a compound of formula (I). The compounds of the formula ArCOOH can be prepared by methods well known to those skilled in the art.

3. The reaction of a compound $ArCH_2L$ (wherein Ar is as hereinbefore defined and L is a leaving group) with a compound of the formula (IV) as hereinbefore defined. Suitable leaving groups are those defined by J. March, vide supra, pages 325–331, and include halogens such as chlorine and bromine and sulfonic acid derivatives such as p-toluenesulfonate. The reaction is suitably carried out in an appropriate solvent, such as a dipolar aprotic solvent or alcohol at a non-extreme temperature, for example 50°–100°. The compounds of the formula $ArCH_2L$ can be prepared by methods well known to those skilled in the art.

There is therefore provided, as a further aspect of the invention, a method for the preparation of a compound of formula (I) comprising any method known for the preparation of analogous compounds, in particular those methods defined in (1) to (3) hereinabove.

The compounds of this invention have biocidal activity, e.g. are toxic to certain living cells which are detrimental to mammals, for example pathogenic organisms and tumor cells.

This toxicity to pathogenic organisms has been demonstrated by activity against viruses (e.g. *Herpes simplex* 1/vero), fungi (e.g. *Candida albicans*), protozoa (e.g. *Eimeria tenella* and *Trichomonas vaginalis*), bacteria (e.g. *Mycoplasma smegmatis* and *Streptococcus pyogenes*), and helminths (e.g. *Nippostrongylus brasiliensis*). The antitumor activity of compounds of formula (I) has been demonstrated in a number of recognized screens and primarily by activity against ascitic P388/0 leukemia.

Preferred compounds of the formula (I) are those which have antitumor activity. The activity against ascitic tumors, including P388/0, is evidenced by reduction of tumor cell number in mammals (for example, mice bearing ascitic tumors) and consequent increase in survival duration as compared to an untreated tumor bearing control group. Antitumor activity is further evidenced by measurable reduction in the size of solid tumors following treatment of mammals with the compounds of this invention compared to the tumors of untreated control tumor bearing animals. Compounds of formula (I) are active against murine tumors such as lymphocytic leukemia P388/0, lymphocytic leukemia L1210, melanotic melanoma B16, P815 mastocytoma, MDAY/D2 fibrosarcoma, colon 38 adenocarcinoma, M5076 rhabdomyosarcoma and Lewis lung carcinoma.

Activity in one or more of these tumor tests has been reported to be indicative of antitumor activity in man (A. Goldin et al. in *Methods in Cancer Research* ed. V. T. DeVital Jr. and H. Busch, 16 165, Academic Press, N.Y. 1979).

There are sublines of P388/0 which have been made resistant to the following clinically useful agents: cytosine arabinoside, doxorubicin, cyclophosphamide, L-phenylalanine mustard, methotrexate, 5-fluorouracil, actinomycin D, cis-platin and bis-chloroethylnitrosourea. Compounds of this invention show potent activity against these drug-resistant tumors using the procedure for P388/0 above.

Compounds of formula (I) have also been found to be active against human tumor cells in primary cultures of lung, ovary, breast, renal, melanoma, unknown primary, gastric, pancreatic, mesothelioma, myeloma, and colon cancer. (As used herein "cancer" is to be taken as synonymous with "malignant tumor" or more generally "tumor" unless otherwise noted.) This is a procedure in which the prevention of tumor cell colony formation, i.e. tumor cell replication, by a drug has been shown to correlate with clinical antitumor activity in man (D. D. Von Hoff et al., *Cancer Chemotherapy and Pharmacology* 6, 265 (1980); S. Salmon and D. D. Von Hoff, *Seminars in Oncology*, 8, 377 (1981)).

Compounds of formula I which have been found to have antitumor activity intercalate in vitro with DNA (this property is determined by viscometric methods using the procedure of W. D. Wilson et al., *Nucleic Acids Research* 4, 2697 (1954)) and a log P as calculated by the method of C. Hansch and A. Leo in *Substituent Constants for Correlation Analysis in Chemistry and Biology*, John Wiley and Sons, New York, 1979, lying in the range between $-2.0$ and $+2.5$.

As has been described above, the compounds of the present invention are useful for the treatment of animals (including humans) bearing susceptible tumors. The invention thus further provides a method for the treatment of tumors in animals, including mammals, especially humans, which comprises the administration of a clinically useful amount of compound of formula (I) in a pharmaceutically useful form, once or several times a day or other appropriate schedule, orally, rectally, parenterally, or applied topically.

In addition, there is provided as a further, or alternative, aspect of the invention, a compound of formula (I) for use in therapy, for example as an antitumor agent.

The amount of compound of formula (I) required to be effective as a biocidal agent will, of course, vary and is ultimately at the discretion of the medical or veterinary practitioner. The factors to be considered include the condition being treated, the route of administration, the nature of the formulation, the mammal's body weight, surface area, age and general condition, and the particular compound to be administered. A suitable effective antitumor dose is in the range of about 0.1 to about 120 mg/kg body weight, preferably in the range of about 1.5 to 50 mg/kg, for example 10 to 30 mg/kg. The total daily dose may be given as a single dose, multiple doses, e.g., two to six times per day, or by intravenous infusion for a selected duration. For example, for a 75 kg mammal, the dose range would be about 8 to 9000 mg per day, and a typical dose would be about 2000 mg per day. If discrete multiple doses are indicated, treatment might typically be 500 mg of a compound of formula I given 4 times per day in a pharmaceutically useful formulation.

While it is possible for the active compound (defined herein as compound of formula (I), or ether, ester, or salt thereof) to be administered alone, it is preferable to present the active compound in a pharmaceutical formulation. Formulations of the present invention, for medical use, comprise an active compound together with one or more pharmaceutically acceptable carriers thereof and optionally other therapeutical ingredients. The carrier(s) must be pharmaceutically acceptable in the sense of being compatible with the other ingredients of the formulation and not deleterious to the recipient thereof.

The present invention, therefore, further provides a pharmaceutical formulation comprising a compound of formula (I) (in the form of the free base, ether, or ester derivative or a pharmaceutically acceptable acid addition salt thereof) together with a pharmaceutically acceptable carrier therefore.

There is also provided a method for the preparation of a pharmaceutical formulation comprising bringing into association a compound of formula (I), an ether, ester, or pharmaceutically acceptable salt thereof, and a pharmaceutically acceptable carrier therefore.

While the antitumor activity of the compounds of formula (I) is believed to reside in the free base, it is often convenient to administer an acid addition salt of a compound of formula (I).

The formulations include those suitable for oral, rectal or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into desired formulations.

Formulations of the present invention suitable for oral administration may be presented as discrete units such as capsules, cachets, tablets or lozenges, each containing a predetermined amount of the active compound; as a powder or granules; or a suspension in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine the active compound in a free-flowing form such as a powder or granules, optionally mixed with a binder, lubricant, inert diluent, surface active or dispersing agent. Molded tablets may be made by molding in a suitable machine, a mixture of the powdered active compound with any suitable carrier.

A syrup may be made by adding the active compound to a concentrated, aqueous solution of a sugar, for example sucrose, to which may also be added any accessory ingredients. Such accessory ingredient(s) may include flavorings, an agent to retard crystallization of the sugar or an agent to increase the solubility of any other ingredient, such as a polyhydric alcohol for example glycerol or sorbitol.

Formulations for rectal administration may be presented as a suppository with a conventional carrier such as cocoa butter.

Formulations suitable for parenteral administration conveniently comprise a sterile aqueous preparation of the active compound which is preferably isotonic with the blood of the recipient. Such formulations suitably comprise a solution of a pharmaceutically and pharmacologically acceptable acid addition salt of a compound of the formula (I) that is isotonic with the blood of the recipient. Thus, such formulations may conveniently contain distilled water, 5% dextrose in distilled water or saline and a pharmaceutically and pharmacologically acceptable acid addition salt of a compound of the formula (I) that has an appropriate solubility in these solvents, for example the hydrochloride, isethionate and methanesulfonate salts, preferably the latter.

Useful formulations also comprise concentrated solutions or solids containing the compound of formula (I) which upon dilution with an appropriate solvent give a solution suitable for parenteral administration above.

In addition to the aforementioned ingredients, the formulations of this invention may further include one or more accessory ingredient(s) selected from diluents, buffers, flavoring agents, binders, surface active agents, thickeners, lubricants, preservatives (including antioxidants) and the like.

The following examples are provided by the way of illustration of the present invention and should in no way be construed as a limitation thereof.

General Comments

All solvents were reagent grade and used without further purification with the following exceptions. THF was dried by distillation from Na/K alloy under nitrogen ($N_2$) and used immediately. Toluene ($PhCH_3$) was distilled from $CaH_2$ under $N_2$ and stored over 3 Å molecular sieves. Chemicals used were reagent grade and used without purification unless noted. The full name and address of the suppliers of the reagents and chemicals is given when first cited. After this, an abbreviated name is used.

Preparative HPLC was carried out on a Water's Prep LC/System 500A machine using two 500 g silica gel ($SiO_2$) cartridges unless otherwise noted. Plugs of $SiO_2$ used for purifications were "flash chromatography" $SiO_2$ (Merck & Co., Inc., Merck Chemical Division, Rahway, NJ, 07065, silica gel 60, 230–400 mesh). In this procedure, an appropriate volume sintered glass funnel was filled approximately ¾ full with the $SiO_2$ and packed evenly by tapping the outside of the funnel. A piece of filter paper was then placed on top of the $SiO_2$ and a solution of the material to be purified applied evenly to the top. Gentle suction through a filter flask moved the eluting solvent through the plug rapidly. The appropriate size fractions were combined as needed and further manipulated.

General procedures are described in detail. Analogous procedures show melting point (mp), recrystallization solvents, and elemental analyses (all elements analyzing within a difference of $\leq 0.4\%$ of the expected value). Any changes to the procedure such as solvent, reaction temperature, reaction time, or workup are noted.

NMR ($^1H$, $^{13}C$), IR, MS data of all new products were consistent with the expected and proposed structures. The positions assigned to structural isomers were unequivocally determined by a number of NMR techniques. All final products were dried in a vacuum oven at 20 mm Hg pressure at the temperature indicated overnight (12–16 h). All temperatures are in degrees Celsius. Other abbreviations used are: room temperature (RT), absolute (abs.), round bottom flask (RB flask), minutes (min), hours (h).

EXAMPLE 1

2-((6-Chrysenylmethyl)amino)-2-methyl-1,3-propanediol 1A. 6-Chrysenecarbaldehyde A 5 L 3-neck flask fitted with overhead mechanical stirrer, thermometer, condenser and $N_2$ line was charged with chrysene (Eastman Kodak Co., Rochester, NY, 14650, 100 g, 0.438 mol) and o-dichlorobenzene (2.5 L). The liquid was warmed until all the large chunks of solid dissolved (80°) and then cooled quickly to give finely divided crystals. After further cooling with a salt-ice bath to 5°, $SnCl_4$ (Aldrich Chemical Co., Milwaukee, WI, 53201, 98%, 228.2 g, 0.876 mol, 102.4 mL) was added in one portion. No temperature change occurred. The reaction mixture was kept below 5°, and 1,1-dichloromethylmethylether (Aldrich, 70.48 g, 0.613 mol, 55.45 mL) was added dropwise over 1 h. The resulting suspension was warmed slowly to 40°. The reaction mixture was then cooled to 10° and hydrolysed by careful addition of 1 L of cold $H_2O$. After 4 h, the layers were separated and the organic layer filtered, dried with anhydrous $Na_2SO_4$ (Mallinckrodt Co., St. Louis, MO, 63147, 100 g) and filtered again. The clear yellow solution was split into 2 portions and each passed through a 500 g plug of $SiO_2$ using $PhCH_3$ as the eluting solvent with 500 mL fractions. This chromatography separated unreacted chrysene (3 g) from the aldehyde and a more polar product. Fractions containing the aldehyde were combined and the $PhCH_3$ removed. Crystals formed during this process and were removed periodically by filtration. After drying (at 60°) the yield of 6-chrysenecarbaldehyde was 89.46 g (79.7%) mp 167°–169°, (C,H), (lit. 168°, N. P. Buu Hoi, J. P. Hoffinger, and P. Jacquignon, *Bull. Soc. Chim. Fr.* 3808 (1968)).

1B.
2-((6-Chrysenylmethyl)amino)-2-methyl-1,3-propanediol hydrochloride

To a 2 L Erlenmeyer flask was added 6-chrysenecarbaldehyde (21.2 g, 82.7 mmol), 2-amino-2-methyl-1,3-propanediol (Aldrich, 9.13 g, 86.8 mmol), p-toluenesulfonic acid.$H_2O$ (Eastment, 0.5 g, 2.5 mmol), and PhCH$_3$ (500 mL). The mixture was warmed to reflux for a few minutes and H$_2$O (2-3 mL) was driven off. The resulting golden colored solution was allowed to cool to RT, diluted with abs. EtOH (500 mL) and stirred overnight. NaBH$_3$CN (Aldrich, 95%, 2.51 g, 42 mmol) was added to the reaction. After the NaBH$_3$CN dissolved, an indicator (bromocresol green, Eastman, 5 mg) was added. To the resulting blue solution was added 5 drops of 1M ethanolic HCl every 15 min. After 3 days the indicator turned green then yellow and a voluminous white precipitate was present in the flask. To the flask was then added 1M ethanolic HCl (10 mL). The reaction was diluted to 4 L with abs. Et$_2$O and stirred for 1 h. The precipitate was then filtered through a medium porosity glass fritted funnel and pressed dry. The filter cake was washed thoroughly with 20% HCl (5×250 mL), pressed dry and then washed with CH$_2$Cl$_2$ (4×500 mL), pressed and sucked dry. The solid was dissolved in abs. EtOH (1400 mL). 1M ethanolic HCl (1 mL) and 5 g of Calgon ® (a trademark of Calgon Corporation, a subsidiary of Merck and Co., Pittsburgh, PA, 15230) brand of activated charcoal were added, and the mixture boiled and filtered through a pad of Celite ® (a trademark of Johns Manville Co., P. O. Box 5108, Denver, CO, 80217) brand of filtered aid. The clear yellow solution was concentrated to 500 mL and diluted to 2 L with abs. Et$_2$O which was then filtered to give the crude product. Further crystallization (2x) from CH$_3$OH/Et$_2$O (1:3) gave 18.07 g (57.2%) of 2-((6-chrysenylmethyl)amino)-2-methyl-1,3-propanediol hydrochloride mp 241°-243° (dec), (C,H,Cl,N).

1C.
2-((6-Chrysenylmethyl)amino)-2-methyl-1,3-propanediol methanesulfonate To a 12 L RB flask equipped with overhead stirrer, condenser, thermometer, and Dean-Stark trap was added chrysene-6-carbaldehyde (Cambridge Chemical, Inc., 202 E. Smith St., Milwaukee, WI, 53207, 260 g, 1.01 mol), 2-amino-2-methyl-1,3-propanediol (Aldrich, 213 g, 2.03 mol), p-toluenesulfonic acid monohydrate (Aldrich, 20.8 g, 0.104 mol) and PhCH$_3$ (3.8 L). The mixture was stirred at reflux with removal of H$_2$O for 2 H (or until no H$_2$O is collected). The mixture was cooled to RT and diluted with abs. EtOH (3.8 L). Solid NaBH$_4$ (MCB Manufacturing Chemists, Inc., 2909 Highland Ave., Cincinnati, OH, 45212, 46 g, 1.22 mol) was added in portions to the stirred mixture with the temperature maintained at 25°-30° by external cooling. After the addition was completed, the reaction was stirred an additional 3 h at RT. The reaction mixture was then concentrated under vacuum to a volume of 800 mL keeping the flask temperature at ≦40°. The slurry was diluted with H$_2$O (6 L) and cooled to 5°.

The solid was removed by filtration and washed with H$_2$O (2×1.5 L).* The solid was then suspended in a mixture of SD3A (US Industrial Chemicals Co., a Division of National Distillers and Chemical Corp., 99 Park Ave., New York, NY, 10016, 2.5 L) and methanesulfonic acid (Morton Thiokol, Inc.-Alfa Products, PO Box 299, 152 Andover Street, Danvers, MA, 01923, 107.2 g, 1.12 mol). The resulting solution was filtered and diluted with 5 L of PhCH$_3$. After crystallization overnight at RT, the mixture was cooled at 5° for 1 h and filtered. The solid was washed with PhCH$_3$ (500 mL) and dried to give 417 g (93%) (after a second crop obtained from the filtrate was added) of 2-((6-chrysenylmethyl)amino-2-methyl-1,3-propanediol methanesulfonate mp 239°-240° (dec), (C,H,N,S).

*Note: In the subsequent procedures referring to this method, the particular compound was then suspended in either abs. EtOH or CH$_3$OH then either ethanolic HCl or methanesulfonic acid was added. After slight warming and filtration, the resulting solution was diluted with Et$_2$O, hexane, or PhCH$_3$. The precipitate which formed was filtered and then recrystallized to give the desired compound.

1D.
2-((6-Chrysenylmethyl)amino)-2-methyl-1,3-propanediol

To a rapidly stirred solution of 2-((6-chrysenylmethyl)amino)-2-methyl-1,3-propanediol hydrochloride (1B, 20 g, 52.36 mmol) in a mixture of CH$_3$OH (200 mL) and H$_2$O (800 mL) was added dropwise over 10 min a 1N NaOH solution (55 mL). The resulting white precipitate was filtered and washed with warm H$_2$O (4×500 mL) and then with Et$_2$O (1 L), sucked dry and placed in a vacuum oven overnight. A total of 17.43 g (96.4%) of 2-((6-chrysenylmethyl)amino)-2-methyl-1,3-propanediol mp 200°-202°, (C,H,N) was obtained.

1E.
2-((6-Chrysenylmethyl)amino)-2-methyl-1,3-propanediol lactate

A mixture of 2-((6-chrysenylmethyl)amino)-2-methyl-1,3-propanediol free base (1D) (3.45 g, 10 mmol) and lactic acid (Fisher Scientific Co., 711 Forbes Ave., Pittsburgh, PA, 15219, 85% liquid, 1.04 g, 10 mmol) in CH$_3$OH (500 mL) was brought to reflux and filtered through a glass fritted funnel. The solvent was removed by rotary evaporation to give a crude white solid. This was crystallized (CH$_3$OH/Et$_2$O) 3x to give 1.84 g (42.2%) of 2-((6-chrysenylmethyl)amino)-2-methyl-1,3-propanediol lactate mp 163°-164°. (C,H,N).

1F.
2-((6-Chrysenylmethyl)amino)-2-methyl-1,3-propanediol.⅓citrate

A mixture of 2-((6-chrysenylmethyl)amino)-2-methyl-1,3-propanediol free base (1D, 3.45 g, 10 mmol) and citric acid (Sigma Chemical Co., P. O. Box 14508, St. Louis, MO, 63178, 1.92 g, 10 mmol) in CH$_3$OH (500 mL) was warmed until it dissolved then filtered through a glass fritted funnel. The solvent was then removed to give a crude white solid. This was boiled with abs. EtOH (2×300 mL) and filtered to give a white solid. This was then recrystallized 2x (CH$_3$OH/Et$_2$O) filtered and dried overnight in a vacuum oven to give 1.24 g of 2-((6-chrysenylmethyl)amino)-2-methyl-1,3-propanediol.⅓citrate mp 146°-151°, (C,H,N).

1G.
2-((6-Chrysenylmethyl)amino)-2-methyl-1,3-propanediol-2-hydroxyethanesulfonate 2-((6-chrysenylmethyl)amino)-2-methyl-1,3-propanediol methanesulfonate (1C, 10.0 g, 26.63 mmol) was neutralized with 1N NaOH (30 mL) in CH$_3$OH/H$_2$O (200/800 mL) as in procedure 1D. The white solid which formed was filtered, washed successively with warm H$_2$O (3×500 mL), CH$_3$OH (200 mL). and abs. Et$_2$O (2×500 mL), sucked semi-dry and the resuspended in CH$_3$OH (500 mL). To this was added a 0.43M aqueous solution of 2-hyroxyethanesulfonic acid (30 mL). Slight warming gave a solution which was then filtered. The solvent was removed by rotary evaporation to give a wet white solid. This was triturated with dry Et$_2$O, filtered, and recrystallized 3x from EtOH- /Et₂O to give 8.8 g (70.4%) of 2-((6-chrysenylmethyl)amino)-2-methyl-1,3-propanediol 2-hydroxyethanesulfonate, mp 212°–213°, (C,H,N,S).

EXAMPLE 2

2-((6-Chrysenylmethyl)amino)-2-hydroxymethyl-1,3-propanediol hydrochloride

Using the reductive amination procedure described in 1B, 6-chrysenecarbaldehyde (1A) and tris(hydroxymethyl)aminomethane (Aldrich) gave 2-((6-chrysenylmethyl)amino)-2-hydroxymethyl-1,3-propanediol hydrochloride, mp 238°–239° (dec), (CH₃OH/Et₂O), (C,H,Cl,N).

EXAMPLE 3

2-((6-Chrysenylmethyl)amino)-2-ethyl-1,3-propanediol hydrochloride

Using the reductive amination procedure described in 1B, 6-chrysenecarbaldehyde (1A) and 2-amino-2-ethyl-1,3-propanediol (Aldrich) gave 2-((6-chrysenylmethyl)amino)-2-ethyl-1,3-propanediol hydrochloride, mp 241°–243° (dec), (EtOH/Et₂O), (C,H,Cl,N).

EXAMPLE 4

2-((12-Chloro-6-chrysenyl)methyl)amino)-2-methyl-1,3-propanediol

4A. 12-Chloro-6-chrysenecarbaldehyde

6-Chlorochrysene (Cambridge Chemical, Inc., 70 g, 0.266 mol) was formylated according to the procedure outlined in 1A, except that $CH_2Cl_2$ (2.5 L) was used as the reaction solvent. Chromatography on a plug of $SiO_2$ (1 kg) using EtOAc as the eluting solvent afforded after removal of solvent and drying 19.1 g ( 25%) of 12-chloro-6-chrysenecarbaldehyde mp 255°–257°, (EtOAc).

4B.
2-((12-Chloro-6-chrysenyl)methyl)amino)-2-methyl-1,3-propanediol methanesulfonate.⅓H₂O Using the reductive amination procedure outlined in 1C, 12-chloro-6-chrysenecarbaldehyde (4A) and 2-amino-2-methyl-1,3-propanediol (Aldrich) gave 2-(((12-chloro-6-chrysenyl)methyl)amino)-2-methyl-1,3-propanediol methanesulfonate.⅓H₂O mp 233°–233.5° (dec), (EtOH/Et₂O), (C,H,Cl,N,S).

EXAMPLE 5

(+−)-(2R*,3RS*,4R*)-3-((6-Chrysenylmethyl)amino)-3-methyl-2,5-pentanediol

5A. 3-Methyl-3-nitro-2,4-pentanediols

Solid NaOH (Mallinckrodt, 286 mg, 7.15 mmol) was added to a solution of 3-nitro-2-butanol (Aldrich, 59.6 g, 0.50 mol) and acetaldehyde (Eastman 132 g, 1.50 mol) in anhydrous DMSO (MCB, 100 mL). The reaction was stirred under N₂ for 5 days. Glacial acetic acid (0.5 mL) was then added to the solution. The solvent was then removed by rotary evaporation, (45° C. bath temperature) to give a yellow liquid. This was diluted with H₂O (200 mL) and extracted with $CH_2Cl_2$ (5×200 mL). The combined $CH_2Cl_2$ extracts were washed sequentially with H₂O (50 mL) and satd. NaCl (50 mL), dried (MgSO₄) and filtered. Volatile components were removed from the filtrate under vacuum (first at aspirator vacuum then at 0.1 mm (bath temperature of 50°–135°)) leaving a viscous yellow liquid (53.0 g, 64%). This was mixed with EtOAc/hexane (1:1) (50 mL) and subjected to flash chromatography on $SiO_2$ (1.5 kg), using 11 L of EtOAc/hexane (1:1) as the eluting solvent and collecting 500 mL fractions. Appropriate fractions were combined and the solvent removed by rotary evaporation to give a total of 43.5 g (53%) of the diastereomeric mixture of 3-methyl-3-nitro-2,4-pentanediols (two meso forms and a dl pair, easily distinguished by NMR in DMSO-d₆).

5B. meso-3-Nitro-3-methyl-2,4-pentanediol and

5C.
(+−)(2R*,3RS,4R*)-3-Nitro-3-methyl-2,4-pentanediol

The chromatographic process described above gave partial separation of the diasteromers. The early fraction (500 mL) gave 13.1 g one of the meso-3-nitro-3-methyl-2,4-pentanediols (5B) as a colorless solid mp 60°–61° (C,H,N). The remaining fractions were combined to give 38.3 g of the isomeric mixture containing both the meso- and dl-compounds. Recrystallization from EtOHc/hexane (300 mL, 2:1) gave 27.8 g of a 4:1 ratio of (+−)(2R*,3RS,4R*)-3-nitro-3-methyl-2,4-pentanediol (5C) and the other of the meso-3-nitro-3-methyl-2,4-pentanediols mp 79°–86° (C,H,N). These two materials were then used without further purification.

5D.
(+−)(2R*,3RS,4R*)-3-Amino-3-methyl-2,4-pentanediol acetate

To a solution of 3-methyl-3-nitro-2,4-pentanediols (5C, 16.3 g, 0.1 mol; the 4:1 mixture of dl pair to one meso form described above) in 95% EtOH (150 mL) was added glacial acetic acid (19 mL) and 10% Pd/C (MCB, 2.0 g). The reduction was carried out in a Parr apparatus at 50 psi of H₂ during a 70 h period at RT. The catalyst was removed by filtration through a Millipore ® filter and the solvent removed under vacuum (RT, 2 days). The viscous, colorless syrup was dissolved in abs. EtOH (30 mL). While slightly warm, the solution was made cloudy by adding anhydrous Et₂O (100 mL) and was then placed in a refrigerator. Colorless crystals formed over two days which were filtered, washed with Et₂O and dried in a vacuum oven (at RT). The yield of pure (+−)-(2R*,3RS,4R*)-3-amino-3-methyl-2,4-pentanediol acetate (as shown by NMR in DMSO-d₆) was 12.8 g mp 110.5°–112° (C,H,N). USSR Pat. No. 521,272 (CA 85:177498) mentions 3-amino-3-methyl-2,4-pentanediol as an intermediate but no synthetic details, physical properties, or stereochemistry was presented in the abstract.

5E. meso-3-Amino-3-methyl-2,4-pentanediol acetate

Using the procedure described in 5D, meso-3-methyl-3-nitro-2,4-pentanediol(5B, undetermined configuration) gave meso-3-amino-3-methyl-2,4-pentanediol acetate (53%), mp 137°–138°, (C,H,N).

5F.
(+−)(2R*,3RS,4R*)3-(6-Chrysenylmethylamino)-3-methyl-2,5-pentanediol methanesulfonate To a RB flask was added (+−)(2R*,3RS,4R*)-3-amino-3-methyl-2,4-pentanediol acetate (5D) and an equimolar amount of NaOCH₃ (MCB) and CH₃OH (100 mL). After brief warming to aid solution, the solvent was removed by rotary evaporation and after addition of chrysene-6-carbaldehyde (1A), the reaction run following the normal reductive amination procedure outlined in 1C to give (+−)(2R*,3RS,4R*)3-((6- chrysenylmethylamino)-3-methyl-2,5-pentanediol methanesulfonate mp 182°-183 (dec), (EtOH/Et2O), (C,H,N,S).

EXAMPLE 6

(+ −)(2R*,3S*)-2-((6-Chrysenylmethyl)amino)-2-methyl-1,3-butanediol 6A. (+ −)(2R*,3S*)-2-Methyl-2-nitro-1,3-butanediol and 6B. (+ −)(2R*,3R*)-2-Methyl-2-nitro-1,3-butanediol To a mixture of 2-nitro-1-propanol (Aldrich, 63.0 g, 0.60 mol) and acetaldehyde (Eastman, 39.6 g, 0.90 mol) cooled in an ice bath under N2 was added cold H2O (40 mL) and calcium hydroxide (200 mg). The mixture was allowed to warm to RT over 2 h and then stirred for 68 h. The resulting solution was neutralized with excess solid CO2. The mixture was stirred for 1 h before filtration through a Millipore ® filter. The filtrate was then concentrated under vacuum at 35°. The residue, a viscous syrup partially crystallized on drying under vacuum (0.1 mm, RT, 48 h) was then triturated with cold Et2O (35 mL). Solid white crystals which formed were collected by filtration, washed with cold Et2O (3×15 mL) and dried under vacuum (0.1 mm, RT) to give 34.1 g of material, judged by NMR to be (+ −)(2R*,3S*)-2-methyl-2-nitro-1,3-butanediol (6A) (purity >97%), racemic). After recrystallization, the diastereomeric purity was >99%, mp 78.5°-81° (lit. 78°; cf. Beil 1, 482, in Henry, Bull. Soc. Chim. Fr. [3] 15, 1224), (C,H,N). The original filtrate (including washes) was concentrated under vacuum to a pale yellow liquid which was subjected to flash chromatography as follows: The sample was mixed with hexane/EtOAc (2:1, 100 mL) and added to a column of dry SiO2 (1.5 kg). The column was eluted with hexane/EtOAc (2:1, 12 L) then hexane/EtOAc (1:1, 6 ) while 500 mL fractions were collected. Appropriate fractions were combined. Pure product was found in the final 8 L; yield, 38.7 g of viscous syrup, judged by NMR to be 1:1 mixture of the two racemic diastereomers (6A and 6B), (C, H, N).

This and another batch of the 1:1 diasteriomeric mixture of 6A and 6B (prepared as described above) were combined (67 g, total) and subjected to successive liquid-liquid partitioning between H2O and EtOAc to give pure samples (99% on the basis of NMR and HPLC (Hamilton PRP-1 column using 3.5% aqueous acetonitrile as the mobile phase)) of (+ −0)(2R*,3S*)-2-methyl-2-nitro-1,3-butanediol (6A) (24.9 g, k'=4.3, mp 79°-81°, C, H, N) and (+ −)(2R*,3R*)-2-methyl-2-nitro-1,3-butanediol (6B) (15.8 g, k'=2.1, C, H, N, a colorless, viscous liquid).

6C.
(+ −)(2R*,4S*,5R*)-4,5-dimethyl-5-nitro-2-phenyl-1,3-dioxane and 6D.
(+ −)(2R*,4S*,5S*)-4,5-dimethyl-5-nitro-2phenyl-1,3-dioxane The relative configurations of the two diastereomeric pairs (6A and 6B) were unequivocably assigned on the basis of comparative NMR analysis of the respective cyclic acetals derived from benzaldehyde. Thus, 6A, (1.49 g, 0.01 mol) and benzaldehyde (Mallinckrodt, 1.06 g, 0.01 mol) were condensed in benzene in the presence of a catalytic amount of p-toluenesulfonic acid (Fisher) with azeotropic removal of water (according to the method of H. Piotrowska, B. Serafin and T. Urbanski, Tetrahedron 109, 379 (1963)). After successive washing with satd. NaHCO3 solution, drying (MgSO4), filtration, and removal of the benzene by rotary evaporation, a pale yellow solid was obtained. A solution of this product in ethanol at 0° C. provided an oil which was isolated by decanting the mother liquor and drying under vacuum (0.1 mm, RT). The yield was 1.48 g (62%) of (+ −)(2R*,4S*,5R*)-4,5-dimethyl-5-nitro-2-phenyl-1,3-dioxane (6C) (C, H, N).

Similarly prepared from 6B and benzaldehyde was (+ −)(2R*,4S*,5S*)-4,5-dimethyl-5-nitro-2-phenyl-1,3-dioxane (6D) (74%) (C, H, N).

6E. (+ −)(2R*,3R*)-2-Amino-2-methyl-1,3-butanediol acetate

Using the procedure described. for 5D. (+ −)(2R*,3R*)-2-methyl-2-nitro-1,3-butanediol (6B) gave (+ −)(2R*,3R*)-2-amino-2-methyl-1,3-butanediol acetate (97%) mp 117°-121° (C, H, N).

6F. (+ −)(2R*, 3S*)-2-Amino-2-methyl-1,3-butanediol acetate

Using the procedure described for 5D (+ −)(2R*,3S*)-2-methyl-2-nitro-1,3-butanediol (6A) gave (+ −)(2R*,3S*)-2-amino-2-methyl-1,3-butanediol acetate (93%) mp 163°-165° (C, H, N).

6G.
(+ −)(2R*,3S*)-2-(6-Chrysenylmethylamino)-2-methyl-1,3-butanediol hydrochloride.⅓H2O To a RB flask was added (+ −)(2R*,3S*)-2-amino-2-methyl-1,3-butanediol acetate (6F) and an equimolar amount of sodium methoxide (MCB) and CH3OH (100 mL). After warming, the solvent was removed by rotary evaporation, and after addition of chrysene-6-carbaldehyde (1A) the reaction run following the normal reductive amination procedure outlined in 1B to give (+ −)(2R*,3S*)-2-((6-chrysenylmethyl)amino)-2-methyl-1,3-butanediol hydrochloride.⅓H2O mp 238°-239° (dec), (EtOH/Et2O), (C, H, Cl, N).

6H.
(+ −)(2R*,3S*)-2-((6-Chrysenylmethyl)amino)-2-methyl-1,3-butanediol methanesulfonate Using the reductive amination procedure outlined in 1C, the two intermediates in 6G gave (+ −)(2R*,3S*)-2-((6-chrysenylmethyl)amino)-2-methyl-1,3-butanediol methanesulfonate mp 220°-221° (dec), (EtOH/Et2O), (C, H, N, S).

EXAMPLE 7

(+ −)-(2R*,3R*)-2-((6-Chrysenylmethyl)amino)-2-methyl-1,3-butanediol hydrochloride Using the procedure outlined for 6G, chrysene-6-carbaldehyde (1A) and (+ −)(2R*,3R*)-2-amino-2-methyl-1,3-butanediol acetate (6E) gave (+ −)-(2R*,3R*)-2-((6-chrysenylmethyl)amino)-2-methyl-1,3-butanediol hydrochloride mp 236°-237.5° (dec), (CH3OH/Et2O), (C, H, Cl, N).

EXAMPLE 8

2-((6-Chrysenylmethyl)amino)-2-ethoxymethyl-1,3-propanediol

8A.
3,5-Diphenyl-7a(7H)-ethoxymethyl-1H,3H,5H-oxazolo(3,4-c)oxazole

A mechanically stirred 60% dispersion of NaH in mineral oil (Alfa, 34.0 g, 0.85 mol) was washed with dry hexane to remove the oil and suspended in dry DMF (300 mL9. To the mixture was added a solution of 3,5-diphenyl-1H,3H,5H-oxazolo(3,4-c)oxazole-7a(7H)-methanol (208.2 g, 0.7 mol, prepared by the method of J. Pierce et al., *J. Amer. Chem. Soc.* 73 2595 (1951)) in dry DMF (300 mL) keeping the reaction mixture between 30°–35°. The salt suspension was stirred at RT for 60 min, diluted with dry DMF (200 mL) to facilitate stirring, cooled, then treated with ethyl iodide (Aldrich, excess) at such a rate that the reaction temperature was between 20°–35°. The mixture was stirred at RT for 2 h, then cautiously treated with abs. EtOH (30 mL). The resulting mixture was diluted with Et$_2$O (2.5 L) and the resulting solids removed by filtration. The solvent was then remoed using a rotary evaporator to give 229.5 g of a yellow oil containing both starting material and desired product. A solution of the oil in chloroform was mixed with SiO$_2$ (200 g) and the solvent removed. The solid was then added to a column of SiO$_2$ (800 g). Elution with the EtOAc/hexane (1:3.5) gave 139.7 g (61.3%) of 3,5-diphenyl-7a(7H)-ethoxymethyl-1H,3H,5H-oxazolo-(3,4-c)oxazole. An analytical sample was obtained by recrystallization from hexane, mp 83.5°–85°, (C, H, N). The bulk of the material was used without further purification.

8B. 2-Amino-2-ethoxymethyl-1,3-propanediol hydrochloride.¼H$_2$O 3,5-Diphenyl-7a(7H)-ethoxymethyl-1H,3H,5H-oxazolo(3,4-c)oxazole (8A, 136 g, 0.42 mol) was dissolved in 6N HCl (400 mL) and the resulting solution stirred 1.5 h at RT. After extraction with Et$_2$O (2×200 mL) to remove benzaldehyde, the aqueous solution was concentrated on a rotary evaporator to give a colorless oil. This was cooled in an ice bath to facilitate crystallization. The solid which formed was slurried with cold CH$_3$CN, filtered, then washed with Et$_2$O and dried in a vacuum oven at RT to give 71 g (89%) of 2-amino-2-ethoxymethyl-1,3-propanediol hydrochloride.¼H$_2$O mp 78°–79°, (C, H, Cl, N).

8C.
2-((6-Chrysenylmethyl)amino)-2-ethoxymethyl-1,3-propanediol hydrochloride To a RB flask was added 2-amino-2-ethoxymethyl-1,3-propanediol hydrochloride.¼H$_2$O (8B) and an equimolar amount of sodium methoxide (MCB) and CH$_3$OH (100 mL). After warming, the solvent was removed by rotary evaporation, and after addition of chrysene-6-carbaldehyde (1A), the reaction run following the normal reductive amination procedure outlined in 1C to give 2-((6-chrysenylmethyl)amino)-2-ethoxymethyl-1,3-propanediol hydrochloride, mp 230°–232° (dec), (CH$_3$OH/Et$_2$O), (C, H, Cl, N).

EXAMPLE 9

3-Methoxy-2-((6-chrysenylmethyl)amino)-2-methyl-1-propanol

9A. 4-Aza-3-hydroxymethyl-3-methyl-1-oxaspiro[4.5]decane

A solution of 2-amino-2-methyl-1,3-propanediol (Aldrich, 303.4 g, (3.0 mol), cyclohexanone (Fisher, 294.5 g, 3.0 mol) and PhCH$_3$ (400 mL) was refluxed for approximately 2 h with azeotropic removal of H$_2$O. The material which crystallized from the PhCH$_3$ on cooling was recrystallized 2X from hexane to give 444.4 g of 4-aza-3-hydroxymethyl-3-methyl-1-oxaspiro[4.5]decane (80%) mp 52°–54°, (C, H, N).

9B.
4-Aza-3-methoxymethyl-3-methyl-1-oxaspiro[4.5]decane

A mechanically stirred 60% dispersion of NaH in mineral oil (Alfa, 75 g, 1.9 mol) was washed with dry hexane to remove the oil and suspended in dry DMF (200 mL). To the mixture was added a solution of 4-aza-3-hydroxymethyl-3-methyl-1-oxaspiro[4.5]decane (9A, 27.8 g, 1.5 mol) in dry DMF (200 mL) keeping the reaction mixture temperature between 30°–35°. Small amounts of DMF were added as necessary to facilitate stirring. The mixture was stirred at RT for 1.5 h, then cooled and treated with methyl iodide (Fisher, 234.2 g, 102.7 mL, 1.65 mol) keeping the reaction temperature between 20°–30°. The mixture was stirred 2 h at RT and slowly treated with abs. EtOH (40 mL), then diluted with dry Et$_2$O (3 L). The reaction mixture was filtered, and the solvent removed by rotary evaporation. The residue was then fractionally distilled to give 209.7 g (70.3%) of 4-aza-3-methoxymethyl-3-methyl-1-oxaspiro[4.5]decane as a colorless liquid bp 114°/14 mm, (C, H, N).

9C. 2-Amino-3-methoxy-2-methyl-1-propanol

A solution of 4-aza-3-methoxymethyl-3-methyl-1-oxaspiro[4.5]decane (9B, 299 g, 1.5 mol) and 6N HCl (500 mL) was refluxed for 60 min. On cooling, two layers formed, the upper one containing cyclohexanone was removed by extraction with Et$_2$O (2×400 mL). The lower aqueous layer was concentrated on a rotary evaporator to give a syrup which then was treated with excess 50% NaOH. The resulting slurry was extracted with Et$_2$O/CH$_2$Cl$_2$ (2:1, 4×500 mL), then with CH$_2$Cl$_2$ (500 mL). The solvent was removed by rotary evaporation to give 198 g of pale oil. Fractional distillation of this oil gave 166 g (93%) of 2-amino-3-methoxymethyl-1-propanol as a colorless oil bp 94°/17 mm, (C, H, N).

9D.
3-Methoxy-2-((6-chrysenylmethyl)amino-2-methyl-1-propanol hydrochloride Using the reductive amination procedure outlined in 1C, chrysene-6-carbaldehyde (1A) and 2-amino-3-methoxy-2-methyl-1-propanol (9C) gave 3-methoxy-2-((6-chrysenylmethyl)amino)-2-methyl-1-propanol hydrochloride mp 233°–234° (dec), (EtOH/Et$_2$O), (C, H, Cl,N).

EXAMPLE 10

(1α,2β,3α)-2-((6-Chrysenylmethyl)amino)-1,3-cyclohexanediol

10A. 1α,2β,3α-2-Amino-1,3-cyclohexanediol acetate

This compound was prepared by the method of F. Lichtenthaler (*Ber.* 96, 845 (1963)), mp 175°–177°, (C, H, N), (lit. 178°–179°, F. Lichtenthaler, (*Ber.* 96, 851 (1963)).

10B. (1α,2β,3α)-2-((6-Chrysenylmethyl)amino)-1,3-cyclohexanediol hydrochloride To a RB flask was added (1α,2β,3α)-2-amino-1,3-cyclohexanediol acetate (10A) and an equimolar amount of NaOCH$_3$ (MCB) and CH$_3$OH (100 mL). After warming, the solvent was removed by rotary evaporation, and after addition of chrysene-6-carbaldehyde (1A), the reaction run following the normal reductive amination procedure outlined in 1C to give (1α,2β,3α)-2-((6-chrysenylmethyl)amino)-1,3-cyclohexanediol hydrochloride mp 280°–282° (dec), (CH$_3$OH/Et$_2$O), (C, H, Cl, N).

10C. (1α,2β,3α)-2-((6-Chrysenylmethyl)amino)-1,3-cyclohexanediol methanesulfonate Using the procedure in 1D, 10B was converted to its free base. Addition of an equivalent of methanesulfonic acid (Alfa, 99.5%) followed by recrystallization (EtOH/Et$_2$O) gave (1α,2β,3α)-2-((6-chrysenylmethyl)amino)-1,3-cyclohexandiol methanesulfonate mp 280°–281° (dec), (C, H, N, S).

EXAMPLE 11

2-((6-Chrysenylmethyl)amino)-2-isopropyl-1,3-propanediol

11A. 2-Isopropyl-2-nitro-1,3-propanediol

A solution of 2-methyl-1-nitropropane (38.7 g, 0.375 mol, prepared by the procedure of N. Kornblum, B Tunbe, and H. Ungnade, *J. Amer. Chem. Soc.*, 76, 3209 (1954)) and NEt$_3$ (Eastman, 3.79 g, 0.0375 mol) in CH$_3$OH (50 mL) was added dropwise 37% aqueous formaldehyde solution (Mallinckrodt, 76.2 g, 0.938 mol) at a rate such that the reaction mixture temperature did not exceed 30°. After 72 h, the solution was concentrated under vacuum and the residue was dissolved in H$_2$O (250 mL). The solution was continuously extracted for 1 h with CH$_2$Cl$_2$ (1 L). The CH$_2$Cl$_2$ solution was dried (MgSO$_4$), filtered, and concentrated to give 53.3 g (87%) of 2-isopropyl-2-nitro-1,3-propanediol, as a waxy, white solid mp 67°–72° C. (lit. mp 87°–88° B. M. Vanderbilt and H. B. Hass, *Ind. Eng. Chem.* 32, 34 (1940). In our hands this procedure failed to give the desired compound).

11B. 2-Amino-2-isopropyl-1,3-propanediol acetate

Using the procedure in 5D, 2-isopropyl-2-nitro-1,3-propanediol (11A) gave a 98% yield of 2-amino-2-isopropyl-1,3-propanediol acetate mp 155°–155.5°. H. S. Broadbent et al., *J. Heterocyclic Chem.*, 13 337 (1975) report the synthesis of this compound as the free base (mp 70°–72°)).

11C. 2-((6-Chrysenylmethyl)amino)-2-isopropyl-1,3-propanediol hydrochloride ¼H$_2$O To a RB flask was added 2-amino-2-isopropyl-1,3-propanediol acetate.¼H$_2$O (11B) and an equimolar amount of sodium methoxide (MCB) and CH$_3$OH (100 mL). After warming, the solvent was removed by rotary evaporation and after addition of chrysene-6-carbaldehyde (1A), the reaction run following the normal reductive amination procedure outlined in 1B to give 2-((6-chrysenylmethyl)amino)-2-isopropyl-1,3-propanediol hydrochloride.H$_2$O mp 223°–223.5° (dec), (EtOH/Et$_2$O), (C, H, Cl, N).

EXAMPLE 12

2-((6-Chrysenylmethyl)amino)-2-methyl-1.4-butanediol

12A. Ethyl N-benzylidene-1-alaninate

Ethyl N-benzylidene-1-alaninate was prepared according to the general procedure of G. Stork et al., *J. Org. Chem.* 41 349 (1976), bp 98°–100°/0.4 mm (lit. 100°/0.3 mm, A. Calcagni et al., Synthesis 445 (1981)).

12B. 2-(2-Iodoethoxy)tetrahydro-2-H-pyran

Freshly distilled dihydropyran (Aldrich, 59.0 g, 0.7 mol) was added dropwise to a cooled solution of 2-iodoethanol (Aldrich, 98 g, 0.57 mol) in Et$_2$O (1 L) containing 0.1 g of p-toluenesulfonic acid (Eastman). The solution was then stirred for 1 h at 5°. Solid K$_2$CO$_3$ (Mallinckrodt, 5 g) was then added to the reaction mixture and the resulting suspension stirred an additional 1 h at RT. The reaction was then filtered and the remaining solid washed with Et$_2$O (1 L). The organic solutions were combined and concentrated rotary evaporation (in a flask washed with 1% NEt$_3$ in H$_2$O). The crude 2-(2-iodoethoxy)-tetrahydro-2-H-pyran (~100 g, 68.9%) was used without further purification.

12C. Ethyl 2-benzylideneamino-2-methyl-4-((tetrahydro-2H-pyran-2-yl)oxy)butyrate A solution of lithium diisopropylamide was prepared by dropwise addition of n-BuLi (Aldrich 1.6M in hexane, 228 mL, 0.365 mol) to a solution of diisopropylamine (Aldrich, 51.6 g, 0.51 mol) in a mixture of dry THF (700 mL) and dry HMPA (Aldrich, 40 mL) kept at 30°–40°. The solution was then cooled to −70° and a solution of ethyl N-benzylidene-1-alaninate (12A, 74.9 g, 0.365 mol) was added dropwise to the solution allowing the reaction mixture warm to −20° for several min. The resulting red solution was then cooled to −70°. 2-(2-Iodoethoxy)tetrahydro-2-H-pyran (12B, 98.1 g, 0.383 mol) was then added to the solution at such a rate that the temperature in the reaction mixture did not rise above −65°. The solution was allowed to warm slowly to RT and stirred for 14 h. The volume of the solution was reduced to ~300 mL by a stream of dry N$_2$ during the last few hours to facilitate the final workup. The reaction was quenched with satd. NaCl (800 mL9 and diluted with Et$_2$O (800 mL). The Et$_2$O was removed and the aqueous layer extracted with hexane (500 mL). The Et$_2$O and hexane layer were combined and dried (Na$_2$SO$_4$). The solution was filtered and the solvent removed to give 124 g of crude red oil. Bulb to bulb distillation (in 1% aq. NEt$_3$ washed glassware) (210° bath temperature/0.3 mm) gave 95 g of ethyl 2-benzylideneamino-2-methyl-4-((tetrahydro-2H-pyran-2- yl)oxy)-butyrate which was homogeneous by vpc and gave acceptable NMR and mass spectra. It was stored under $N_2$ in the refrigerator and was used without further purification.

12D. 2-Benzylamino-2-methyl-4-((tetrahydro-2H-pyran-2-yl)oxy)butanol

A solution of ethyl 2-benzylideneamino-2-methyl-4-((tetrahydro-2H-pyran-2-yl)oxy)butyrate (12C, 100.0 g, 0.3 mol) in THF (100 mL) was added slowly to a suspension of lithium aluminum hydride (Alfa, 22.77 g, 0.6 mol) rapidly stirred in dry THF (1 L) at such a rate to maintain a gentle reflux. After addition was complete the mixture was refluxed for 4 h. The reaction mixture was cooled and treated successively with $H_2O$ (23 mL), 15N NaOH (23 mL) and $H_2O$ (45 mL). The solid was removed by filtration and washed with THF (200 mL). The organic layers were combined and concentrated by rotary evaporation to give 2-benzylamino-2-methyl-4-((tetrahydro-2H-pyran-2-yl)oxy)butanol (81.1 g, 92.0%) as a thick oil which was used without further purification.

12E. 2-Benzylamino-2-methyl-1,4-butanediol

The crude 2-benzylamino-2-methyl-4-((tetrahydro-2H-pyran-2-yl)oxy)butanol (12D, 80.1 g, 0.273 mol) was dissolved in 3N HCl (128 mL). After 5 min the mixture was washed with $Et_2O$ (200 mL). The aqueous solution was concentrated by rotary evaporation to give a thick oil which was cooled and basified with excess 50% NaOH. The oily amine which formed was extracted with $Et_2O$ (3×200 mL). The $Et_2O$ extracts were combined and concentrated to give 63.6 g of a thick oil. Distillation gave 49.8 g (94%) of 2-benzylamino-2-methyl-1,4-butanediol as a pale yellow oil (bp 168°–170°/0.35 mm) (C, H, N)

12F. 2-Amino-2-methyl-1,4-butanediol hydrochloride

2-Benzylamino-2-methyl-1,4-butanediol (12E, 31.08 g, 0.149 mol) was dissolved in 95% EtOH (240 mL) containing conc. HCl (21 mL, 0.25 mol) and 5% Pd/C (10.0 g) and reduced in a Parr apparatus at 40 psi over 37 h at RT. The catalyst was then removed by filtration and the solvent removed by rotary evaporation (bath at 60°) to give 20.91 g of 2-amino-2-methyl-1,4-butanediol hydrochloride (90.2%) as a clear, thick, colorless oil with acceptable NMR and mass spectra. It was used without further purification. This compound has been reported as its acetate salt (G. Cardillo et al., Chem. Commun. 1308, 1982), but no data was given. Attempts to duplicate the latter procedure were unsuccessful.

12G. 2-((6-Chrysenylmethyl)amino)-2-methyl-1,4-butanediol hydrochloride.⅓EtOH To a RB flask was added 2-amino-2-methyl-1,4-butanediol hydrochloride (12F) and an equal amount of sodium methoxide (MCB) and enough $CH_3OH$ to form a solution when warmed. The solvent was then removed by rotary evaporation and after addition of chrysene-6-carbaldehyde (1A), the reaction run following the normal reductive amination procedure outlined in 1C to give 2-((6-chrysenylmethyl)amino)-2-methyl-1,4-butanediol hydrochloride.⅓EtOH mp 233°–235° (dec), (EtOH/$Et_2O$) (C, H, Cl, N).

EXAMPLE 13
meso-3-((6-Chrysenylmethyl)amino)-2,4-pentanediol

13A. 3-Nitro-2,4-pentanediol

A solution of nitromethane (Aldrich, 73.3 g, 1.2 mol) and acetaldehyde (Eastman, 158.6 g, 3.6 mol) was cooled in a ice bath. $H_2O$ (80 mL) and $Ca(OH)_2$ (0.40 g) were then added to the flask. The mixture was stirred under $N_2$ for 8 h, neutralized with $CO_2$ and filtered. The filtrate was extracted continuously with $CH_2Cl_2$ (1 L) for 6 h. The $CH_2Cl_2$ extract was concentrated under vacuum to give 114.6 g (77%) of crude 3-nitro-2,4-pentanediols as, a pale yellow syrup. This material was unstable and was used without further purification. Z. Eckstein and T. Urbanski, *Roczniki Chem.* 26, 571 (1952), also report the synthesis and isolation as a crude material of this material.

13B. (2α,4α,5α,6α)-4,6-Dimethyl-5-nitro-2-phenyl-1,3-dioxane

A solution of the crude mixture of 3-nitro-2,4-pentanediols (13A, 115 g, ~0.77 mol) from above, benzaldehyde (Fisher 81.7 g, 0.77 mol) and p-toluenesulfonic acid (Fisher, 1.28 g) in benzene (400 mL) was refluxed for 1.5 h with azeotropic removal of $H_2O$. After removal of the solvent under vacuum, the crude product (a complex mixture) was dissolved in abs. EtOH (150 mL). After 36 h, the crystals that had formed (RT) were collected and dried to give yield 25.8 g, of a 5:1 mixture (based in NMR) of desired product and another isomer (C, H, N). Pure 2α,4',5α,6α-4,6-dimethyl-5-nitor-2-phenyl-1,3-dioxane was obtained after recrystallization from abs. EtOH mp 117.5 –118° (C, H, N).

13C. meso-3-Amino-2,4-pentanediol acetate (2α,4α,5α,6α)-4,6-Dimethyl-5-nitro-2-phenyl-1,3-dioxane was reduced as described in 5D except that the temperature was 50° C. Recrystallization (95% EtOH) gave meso-3-amino-2,4-pentanediol acetate mp 108.5°–109.5°, (C, H, N).

13D. meso-3-((6-Chrysenylmethyl)amino)-2,4-pentanediol methanesulfonate

To a RB flask was added meso-3-amino-3-methyl-2,4-pentanediol acetate (13C) and an equimolar amount of $NaOCH_3$ (MCB) and $CH_3OH$ (100 mL). After warming to aid solution the solvent was removed by rotary evaporation. After addition of chrysene-6-carbaldehyde (1A), the reaction was run following the normal reductive amination procedure outlined in 1C to give meso-3-((6-chrysenylmethyl)amino)-2,4-pentanediol methanesulfonate mp 221–223), ($CH_3OH$/$Et_2O$), (C, H, N, S).

EXAMPLE 14
2-((6-Chrysenylmethyl)amino)-1,3-propanediol methanesulfonate

Using the reductive amination procedure outlined in 1C, chrysene-6-carbaldehyde (1A) and 2-amino-1,3-propanediol hydrochloride (Sigma) gave 2-((6-chrysenylmethyl)amino)-1,3-propanediol methanesulfonate mp 208°–209°, ($CH_3OH$/$Et_2O$), (C, H, N, S).

EXAMPLE 15

2-(((12-Ethyl-6-chrysenyl)methyl)amino)-2-methyl-1,3-propanediol

15A. 12-Ethyl-6-chrysenecarbaldehyde

6-Ethylchrysene (Cambridge Chemical, Inc., 60 g, 0.234 mol) was formylated according to the procedure outlined in 1A, except that $CH_2Cl_2$ (1 L) was used as the reaction solvent. The crude material was chromatographed on a plug of $SiO_2$ (1 kg) using $PhCH_3$ as the eluting solvent, afforded 50.38 g (76%) of 12-ethyl-6-chrysenecarbaldehyde mp 138°–139°, (C, H).

15B. 2-(((12-Ethyl-6-chrysenyl)methyl)amino)-2-methyl-1,3-propanediol methanesulfonate Using the reductive amination procedure outlined in 1C, 12-ethyl-6-chrysenecarbaldehyde (15A) and 2-amino-2-methyl-1,3-propanediol (Aldrich) gave 2-(((12-ethyl-6-chrysenyl)methyl)amino)-2-methyl-1,3-propanediol methanesulfonate mp 189°–192° (dec), (EtOH/$Et_2O$), (C, H, N, S).

EXAMPLE 16

2-((6-Chrysenylmethyl)amino)-2-methyl-1,3-propanediol diacetate

A mixture of 2-((6-chrysenylmethyl)amino)-2-methyl-1,3-propanediol hydrochloride (1B, 5.0 g, 13.1 mmol) and acetylchloride (Aldrich, 5.0 mL, 70.3 mmol) was refluxed in dry THF (200 mL) under $N_2$ for 12 h. The reaction mixture was poured into a satd. $NaHCO_3$ solution (500 mL) and extracted with EtOAc (3×500 mL). The EtOAc layes were combined, dried ($K_2CO_3$) and filtered to give a slightly yellow liquid. The solvent was removed to give an off-white solid. This was recrystallized 3× from $PhCH_3$/hexane (1:1). After filtration and drying, 3.67 g (65.2%) of 2-((6-chrysenylmethyl)amino)-2-methyl-1,3-propanediol diacetate was obtained mp 136°–137.5°, (C, H, N).

EXAMPLE 17

2-(((12-Ethoxy-6-chrysenyl)methyl)amino)-2-methyl-1,3-propanedioil methanesulfonate

17A. 12-Ethoxychrysene-6-carbaldehyde

6-Ethoxychrysene (Cambridge Chemical, Inc., 48 g, 0.176 mol) was formylated according to the procedure outlined in 1A, except that $CH_2Cl_2$ (1 L) was used as the reaction solvent. After isolation, the crude material was chromatographed on a plug of $SiO_2$ (500 g) using $CH_2Cl_2$ as the eluting solvent to give (after removal of solvent and drying) 33.7 g (64%) of 12-ethoxychrysene-6-carbaldehyde mp 173.5°–176°, (C, H).

17B. 2-(((12-Ethoxy-6-chrysenyhl)methyl)amino)-2-methyl-1,3-propanediol methanesulfonate Using the reductive amination procedure described in 1C, 12-ethoxy-6-chrysenecarbaldehyde (17A) and 2-amino-2-methyl-1,3-propanediol (Aldrich) gave 2-(((12-ethoxy-6-chrysenyl)methyl)amino)-2-methyl-1,3-propanediol methanesulfonate mp 202°–204° (dec) (EtOH/$Et_2O$), (C, H, N, S).

EXAMPLE 18

2-((6-Chrysenylmethyl)amino)-2-methylpropanol hydrochloride

Using the reductive amination procedure described in 1C, 6-chrysenecarbaldehyde (1A) and 2-methyl-2-aminopropanol (Aldrich) gave 2-((6-chrysenylmethyl)amino)-2-methyl-1-propanol hydrochloride mp 275°–277° (dec), ($CH_3OH$/$Et_2O$), (C, H, Cl, N).

EXAMPLE 19

2-((3-Chrysenylmethyl)amino)-2-methyl-1,3-propanediol

19A. 2-Acetylchrysene

19B. 3-Acetylchrysene

19C. 6-Acetylchrysene

Friedel-Crafts reaction of chrysene with $AlCl_3$/$CH_3COCl$/$PhNO_2$ gave a mixture of 2-, 3-, and 6-acetylchrysenes (285 g, Cambridge Chemical, Inc.). This was stirred and heated in $CH_2Cl_2$ (400 mL) and then filtered. The insoluble material, 2-acetylchrysene, was washed copiously with $CH_2Cl_2$. The solvent was removed from the filtrate. The resulting solid was dissolved in $PhCH_3$, then the mixture containing the remaining two isomers chromatographed using $PhCH_3$ as eluting solvent on a plug of $SiO_2$ (1 kg). The faster eluting isomer is 6-acetylchrysene while the slower is 3-acetylchrysene. The chromatography gave 132 g of impure 6-acetylchrysene, and 76 g of impure 3-acetylchrysene. These materials were used without further purification. Pure samples of the compounds were obtained by preparative HPLC using $PhCH_3$ as the eluting solvent.

19A. 2-Acetylchrysene mp 25420 –255°, (lit. mp 252°–253°, W. Carruthers, *J. Chem. Soc.* 3486 (1953)) ($PhCH_3$), (C, H), (Rf=0.50, $SiO_2$, $PhCH_3$);

19B. 3-Acetylchrysene mp 160°–161°, (lit. mp 159°, W. Carruthers, *J. Chem Soc.* 3486 (1953)) ($CH_2Cl_2$/MeOH) (C, H), (Rf=0.51, $SiO_2$, $PhCH_3$);

19C. 6-Acetylchrysene mp 141°–142° (lit. mp 141°, W. Carruthers, *J. Chem. Soc.* 3486 (1953)), ($CH_2Cl_2$/MeOH), (C, H), (Rf=0.59, $SiO_2$, $PhCH_3$).

19D. Chrysene-3-carboxylic acid

3-Acetylchrysene (19B) was converted by the method of J van de Kamp, *J Amer. Chem. Soc.* 52, 3704 (1930) to chrysene-3-carboxylic acid mp 302°–304° (dec), (lit, mp 295° (dec), W. Carruthers, *J. Chem. Soc.* 3486 (1953)), (THF/EtoH), (C, H).

19E. Ethyl chrysene-3-carboxylate

By the procedure of P. Arjunan and K. D. Berlin, *Org. Prep. and Procedures* 13 (5), 368 (1981), chrysene-3-carboxylic acid (19D, 18.3 g, 0.067 mol) was converted to ethyl chrysene-3-carboxylate 18.09 g (90%) mp 123°–124°, ($PhCH_3$/hexane), (C, H).

19F. 3-Hydroxymethylchrysene

A solution of ethyl chrysene-3-carboxylate (19E 17.7 g, 0.059 mol) in 40 mL THF was treated with $LiBH_4$ (Morton Thiokol, Inc.-Alfa Products, PO Box 299, 152 Andover St., Danvers, MA 01923, 2.7 g, 0.12 mol) in three portions then refluxed for 3 days. The reaction mixture was poured into ice and acidified carefully to pH 1 with 1N HCl. The precipitate was filtered and recrystallized from THF/hexane to afford 14.98 g (98%) of 3-chrysenemethanol mp 187°–189°, (C, H).

19G. Chrysene-3-carbaldehyde

3-Hydroxymethylchrysene (19F, 14.6 g, 0.057 mol) in $CH_2Cl_2$ (2 L) was treated with $BaMnO_4$ (Aldrich, 29 g, 0.113 mol) and refluxed for 15 h. The reaction mixture was filtered, the solvent removed, and the resulting solid eluted through a plug of $SiO_2$ (500 g) using $PhCH_3$ as the eluting solvent. The appropriate fractions were combined and concentrated to 75 mL. Filtration and drying of the precipitate which formed gave 12.88 g (89%) of chrysene-3-carbaldehyde mp 177°–177.5°, (C, H).

19H. 2-((3-Chrysenylmethyl)amino)-2-methyl-1,3-propanediol methanesulfonate

Using the reductive amination procedure outlined in 1C, chrysene-3-carbaldehyde (19G) and 2-amino-2-methyl-1,3-propanediol (Aldrich) gave 2-((3-chrysenylmethyl)amino)-2-methyl-1,3-propanediol methanesulfonate mp 180°–182° (dec), (EtOH/Et₂O), (C, H, N, S).

EXAMPLE 20

2-((2-Chrysenylmethyl)amino)-2-methyl-1,3-propanediol

20A. Chrysene-2-carboxylic acid

Using the method of J. van de Kamp, *J. Amer. Chem. Soc.* 52, 3704 (1930), except that the oxidation was run at 65° using pyridine as cosolvent to improve the solubility, 2-acetylchrysene (19A) was converted to chrysene-2-carboxylic acid mp 337°–338° (lit. mp 325°–327° (dec), *J. Chem. Soc.* 3486 (1953)), (THF/EtOAc).

20B. Ethyl chrysene-2-carboxylate

By the procedure of P. Arjunan and K. D. Berlin, *Org. Prep. and Procedures* 13(5), 368 (1981), chrysene-2-carboxylic acid (20A, 10.4 g, 0.038 mol) was converted to ethyl chrysene-2-carboxylate 10.5 g (92%) mp 205°–206°, ($PhCH_3$/hexane).

20C. 2-Hydroxymethylchrysene

Ethyl chrysene-2-carboxylate (20B, 10.1 g, 0.034 mol) in THF (500 mL) was treated with $LiBH_4$ (Alfa, 4×0.5 g, 0.092 mol) under gentle reflux for 4 days. The reaction mixture was poured into ice and acidified carefully to pH 1 with 1M HCl. The precipitate was filtered and recrystallized from THF/hexane to afford 8.32 g (95%) of 2-chrysenemethanol mp 261°–262°, (C, H).

20D. Chrysene-2-carbaldehyde

2-Hydroxymethylchrysene (20C, 8.0 g, 0.031 mol) in $CH_2Cl_2$ (2.5 L) was treated with $BaMnO_4$ (Aldrich, 15.9 g, 0.062 mol) and refluxed for 12 h. The reaction mixture was filtered, and concentrated to give a solid, which was then passed through a plug of $SiO_2$ (500 g) using $PhCH_3$ as the eluting solvent. The appropriate fractions were combined and the volume reduced to 75 mL to afford 6.98 g (88%) of chrysene-2-carbaldehyde mp 215°–216.5°, (C, H).

20E. 2-((2-Chrysenylmethyl)aminio-2-methyl-1,3-propanediol methanesulfonate

Using the reductive amination procedure outlined in 1C, chrysene-2-carbaldehyde (20D) and 2-amino-2-methyl-1,3-propanediol (Aldrich) gave 2-((2-chrysenylmethyl)amino)-2-methyl-1,3-propanediol methanesulfonate, mp 225°–227° (dec), (abs. EtOH), (C, H, N, S)

Antitumor Screening Results

Methods for evaluating the antitumor activity of these compounds are essentially those used in the Tumor Panel by the Development Therapeutics Program, Division of Cancer Treatment, National Cancer Institute, A. Goldin, et al., *Methods in Cancer Research*, Vol. XVI, p. 165, Academic Press (1979). Some modifications, in dose level and schedule have been made to increase the testing efficiency.

EXAMPLE 21

Lymphocytic Leukemia P388/0 Test $CD2-F_1$ mice, of the same sex, weighing 20±3 g, are used for this test. Control and test animals are injected intraperitoneally with suspension of $\sim 10^6$ viable P388/0 tumor cells on day 0. In each test, several dose levels whick bracket the $LD_{20}$ of the compound are evaluated; each dose level group contains six animals. The test compounds are prepared either in physiologic saline containing 0.05% Tween 80 or distilled water containing 5% dextrose and are administered intraperitoneally on days 1, 5, and 9 relative to tumor implant. Doses are on a mg/kg basis according to individual animals' body weights. The day of death for each animal is recorded, the median identified for each group and the ratios of median survival time for treated (T)/control (C) groups are calculated. The criterion for activity is $T/C \times 100 \geq 120\%$. Results of P388/0 testing are summarized in Table I below.

TABLE I

| P388/0 SCREENING RESULTS | | | |
|---|---|---|---|
| Compound of Example No. | Optimal Dose (mg/kg) | T/C × 100% (Excluding 30 Day Survivors) | $LD_{20}{}^a$ |
| 1B | 121 | +280 | 140 |
| 1C | 115 | +270 | 105 |
| 2 | 100 | +240 | 100 |
| 3 | 100 | +240 | 100 |
| 6G | 65 | +245 | 53 |
| 18B | 88 | +240 | 80 |
| 19H | 110 | +120 | 150 |
| 6H | 60 | +235 | 60 |
| 7 | 110 | +285 | 100 |
| 9 | 300 | +181 | 425 |
| 10B | 1013 | +205 | (675) |
| 11C | 150 | +220 | 150 |
| 12G | 90 | +270 | 90 |
| 5F | 225 | +255 | 225 |
| 13D | 303 | +200 | 675 |
| 14 | 196 | +270 | 160 |
| 15B | 250 | +130 | 150 |
| 16 | 1012 | +145 | 675 |
| 4B | 180 | +155 | 180 |

$^a$Values in parentheses are the highest non-toxic dose where the $LD_{20}$ was not determined.

EXAMPLE 22

Lymphocytic Leukemia L1210 Test

The protocol for this test is identical to that for P388/0, except that the number of L1210 cells implanted on day 0 is $\sim 10^5$/mouse. The mouse $CD2-F_1$ strain is used, and the criterion for activity is $T/C \times 100 \geq 125\%$. Results of L1210 testing are summarized in Table II below.

TABLE II

| | Screening Results for L1210 | |
|---|---|---|
| Compound of Example No. | Dose (mg/kg) | T/C × 100% Excluding 30 day Survivors |
| 1C | 120 | +252 |

EXAMPLE 23

Melanotic Melanoma B16

B6C3-$F_1$ mice of the same sex, weighing 20±3 g, are used for this test. A suspension of B16 cells is prepared from a non-necrotic portion of solid tumor tissue obtained from a passage mouse. One gram of tumor is homogenized in 9 mL ice-cold Earle's salts solution and filtered through 1000 mesh screen to remove debris. 0.5 mL of the resulting brei is injected intraperitoneally into each animal. Dosing is carried out as in the P388/0 and L1210 tests. Days of death are recorded for a 60 day period and T/C ratio calculated as in the P388/0 and L1210 tests. The criterion for activity is T/C×100>125%. The results of B16 testing are summarized below in Table III.

TABLE III

| | Screening Results for B16 Melanoma | |
|---|---|---|
| Compound of Example No. | Dose (mg/kg) | T/C × 100% Excludong 60 day Survivors |
| 1C | 100 | +146 |
| 6G | 50 | +160 |
| 3 | 70 | +144 |
| 2 | 75 | +144 |
| 18B | 70 | +125 |

EXAMPLE 24

Lewis Lung Carcinoma Test

This tumor arose spontaneously in the lung of a C57B1/6 mouse and is maintained by subcutaneous passage in that strain. The solid tumor is excised aseptically and placed in sterile saline. Pieces of viable tumor tissue are minced finely with scissors and forced through a 200 mesh stainless steel screen to disaggregate the tumor cells into a suspension. $10^6$ Viable cells are injected intravenously into the tail vein of BD-$F_1$, mice of the same sex weighing 20±3 g. In each test, several dose levels which bracket the $LD_{20}$ for the compound are evaluated. Ten animals are included in each dose level group, and twenty animals in the untreated control group. The test compounds are prepared and administered on days 1, 5, and 9 as in the P388/0 protocol. The day of death for each animal is recorded, the median identified for each group and the ratios of median survival time for treated (T)/control (C) groups are calculated. The criterion for activity is T/C×100≧140%. The results of Lewis lung testing are summarized in Table IV.

TABLE IV

| | Screening Results for Lewis Lung | |
|---|---|---|
| Compound of Example No. | Dose (mg/kg) | T/C × 100% Excluding 60 day Survivors |
| 1C | 105 | +191 |

EXAMPLE 25

Colon 38 Carcinoma Test

This chemically-induced tumor arose in a C57B1/6 mouse and is maintained as a solid tumor in that mouse strain. The subcutaneously growing solid tumor is aseptically excised from passage mice and placed in sterile saline. The tumor is trimmed free of visible necrotic and connective tissue, then divided into B 2-3 mm cubes. A cube is implanted subcutaneously in the ventral thoracic region with a sterile trochar on day 0. In each test several dose levels which bracket the $LD_{20}$ for the compound are evaluated. Ten animals are included in each dose level group and thirty animals in the untreated control group. The test compounds are prepared either in physiologic saline containing 0.05% Tween 80 or distilled water containing 5% dextrose and are administered intraperitoneally on days 1, 5 and 9 after tumor implant. Doses are on a mg/kg basis according to individual animals' body weights. At day 20, the animals are sacrificed and the longest (L) and shortest (W) dimensions of each tumor measured with vernier calipers. Tumor weight is calculated from the formula $Lx(W)^2/2$. The criterion for activity is T/C×100≦42%. The results of Colon 38 testing are summarized in Table V.

TABLE V

| | Screening Results for Colon 38 | |
|---|---|---|
| Compound of Example No. | Dose (mg/kg) | T/C × 100% |
| 1C | 120 | 36 |

EXAMPLE 26

M5076 Sarcoma Test

This sarcoma arose as a solid tumor in the ovary of a C57B1/6 mouse and was subsequently converted to the ascitic form for intraperitoneal use. The protocol for this test is identical with that for P388/0. The B6C3-$F_1$ mouse strain is used and the criterion for activity is T/C×100≧125%. Results of M5076 testing are summarized in Table VI below.

TABLE VI

| | Screening Results for M5076 | |
|---|---|---|
| Compound of Example No. | Dose (mg/kg) | T/C × 100% |
| 1C | 105 | +168 |

EXAMPLE 27

Herpes simplex 1/vero Test

Antiviral testing against *Herpes simplex* 1/vero was done using plaque inhibition methods as outlined in P. Collins and D. J. Bauer, *Proc. N.Y. Acad. Sci.* 284, 49 (1977) and by plaque reduction methods as outlined in P. Collins and D. J. Bauer, *J. Antimicrobial Chemotherapy* 3, Supplement A, 73 (1977). The column headings labeled Score, Toxicity, and Zone of Inhibition refer to the plaque inhibition screen while the $IC_{50}$ heading to the plaque reduction screen.

TABLE VII

Results of Antiviral Screening Against *herpes simplex* 1/vero

| Compound of Example No. | Score[A] | Toxicity | Zone of Inhibition[B] | IC$_{50}$[B] |
|---|---|---|---|---|
| 1B | −3 | Y | 43 ST30 | |
| 7 | −4 | Y | | 12 |
| 8C | −4 | Y | | 10.1 |
| 9D | −4 | Y | | 5.6 |
| 11C | −4 | Y | | 3.9 |

[A]Score: 0 = no inhibition, −1 = 1−25% inhibition, −2 = 26−50% inhibition −3 = 51−75% inhibition, −4 = 76−100% inhibition
[B]ST = slight toxicity, T = toxic

EXAMPLE 28

Candida albicans Test

Antifungal testing against *Candida albicans* (CN 1863) was done with slight modifications using a combination of broth and agar dilution assays as outlined in Laboratory Handbook of Medical Mycology, Chapter 6, pages 441−446, M. R. McGinnis, Academic Press, New York, N.Y., 1980

TABLE VIII

Results of Antifungal Testing Against *Candida albicans* (CN1863)

| Compound of Example No. | MIC (mg/L) |
|---|---|
| 1B | 100 |
| 3 | 100 |
| 6G | 100 |
| 18B | 30 |

Medium. Wellcotest ® sensitivity test agar plus 7% lysed horse blood.

Antibacterial Screening

Antibacterial testing against *Mycoplasma smegmatis* (S3264) and *Streptococcus pyogenes* (CN10) was done with slight modifications using standard agar dilution assays as outlined in Manual of Clinical Microbiology Second Ed., E. H. Lennette, E. H. Spaulding and J. P. Truant Eds., American Society for Microbiology, Washington, D.C., 1974

EXAMPLE 29

TABLE IX

Results of Antibacterial Testing Against *Streptococcus pyogenes* (CN10)

| Compound of Example No. | MIC (mg/L) |
|---|---|
| 1B | ≦10 |
| 2 | 10 |
| 3 | 10 |
| 6G | 10 |
| 16 | 10 |
| 18B | ≦3 |

EXAMPLE 30

Mycoplasma smegmatis Test

TABLE X

Results of Antibacterial Screening Against *Mycoplasma smegmatis* (53264)

| Compound of Example No. | MIC (mg/L) |
|---|---|
| 1B | ≦10 |
| 2 | 10 |
| 3 | >100 |
| 6G | ≦3 |
| 16 | 10 |

TABLE X-continued

Results of Antibacterial Screening Against *Mycoplasma smegmatis* (53264)

| Compound of Example No. | MIC (mg/L) |
|---|---|
| 18B | 10 |

EXAMPLE 31

LD$_{50}$ Tests

TABLE XIV

LD$_{50}$ Values for Selected Compounds (IP single dose - CD-1 Male Mouse)

| Compound of Example No. | LD$_{50}$ (mg/kg) |
|---|---|
| 1B | 140 |

EXAMPLE 32

Formulation Examples

| A. TABLET | |
|---|---|
| Compound of Formula I | 500.0 mg |
| Pregelatinized Corn Starch | 60.0 mg |
| Sodium Starch Glycolate | 36.0 mg |
| Magnesium Stearate | 4.0 mg |

The compound of formula (I) is finely ground and intimately mixed with the powdered excipients, pregelatinized corn starch and sodium starch glycolate. The powders are wetted with purified water to form granules. The granules are dried and mixed with the magnesium stearate. The formulation is then compressed into tablets weighing approximately 600 mg each.

| B. TABLET | |
|---|---|
| Compound of formula (I) | 500.0 mg |
| Corn Starch | 70.0 mg |
| Lactose | 83.8 mg |
| Magnesium Stearate | 4.2 mg |
| Polyvinylpyrrolidone | 14.0 mg |
| Stearic Acid | 28.0 mg |

The compound of formula (I) is finely ground and intimately mixed with the powdered excipients, corns starch and lactose. The powders are wetted with a solution of polyvinylpyrrolidone dissolved in purified water and denatured alcohol to form granules. The granules are dried and mixed with the powdered stearic acid and magnesium stearate. THe formulation is then compressed into tablets weighing approximately 700 mg each.

| C. CAPSULES | |
|---|---|
| Compound of formula (I) | 500.0 mg |
| Corn Starch | 50.0 mg |
| Magnesium Stearate | 3.0 mg |

The finely divided compound of formula (I) is mixed with powdered corn starch and wetted with denatured alcohol to densify the powder. The dried powder is mixed with stearic acid and filled into hard-shell gelatin capsules.

| D. SYRUP | |
| --- | --- |
| Compound of formula (I) | 250.0 mg |
| Ethanol | 250.0 mg |
| Glycerin | 500.0 mg |
| Sucrose | 3,500.0 mg |
| Flavoring Agent | q.s. |
| Coloring Agent | q.s. |
| Preserving Agent | 0.1% |
| Purified Water | q.s. to 5.0 mL |

The compound of formula (I) is dissolved in the ethanol, glycerin, and a portion of the purified water. THe sucrose and preserving agent are dissolved in another portion of hot purified water, and then the colouring agent is added and dissolved. The two solutions are mixed and cooled before the flavouring agent is added. Purified water is added to final volume. The resulting syrup is throughly mixed.

| E. IV INJECTION | |
| --- | --- |
| Compound of formula (I) | 5.0 mg |
| Glycerin | q.s. for isotonicity |
| Preservative | 0.1% |
| Hydrochloric Acid or Sodium Hydroxide | as needed for pH adjustment |
| Water for Injection | q.s. to 1 mL |

The compound of formula (I) and preservative is added to the glycerin and a portion of the water for injection. The pH is adjusted with hydrochloric acid or sodium hydroxide. Water for injection is added to final volume and solution is complete after thorough mixing. The solution is sterilized by filtration through a 0.22 micrometer membrane filter and aseptically filled into sterile 10 mL ampules or vials.

What is claimed is:

1. A pharmaceutical composition in the form of a tablet or capsule containing 2-((6-chrysenylmethyl)amino)-2-methyl-1,3-propanediol or a pharmaceutically acceptable salt thereof together with a pharmaceutically acceptable carrier therefor.

2. A tablet or capsule for medicinal use containing 2-((6-chrysenylmethyl)amino)-2-methyl-1,3-propanediol methanesulphonate together with a pharmaceutically acceptable crrier therefor.

3. A sterile pharmaceutical parenteral preparation comprising 2-((6-chrysenylmethyl)amino)-2-methyl-1,3-propanediol or a pharmaceutically acceptable salt thereof together with a pharmaceutically acceptable solvent therefor.

4. A sterile pharmaceutical preparation comprising 2-((6-chrysenylmethyl)amino)-2-methyl-1,3-propanediol methanesulphonate and a pharmaceutically acceptable solvent therefor.

5. The method of reducing the number of cells of a susceptible tumor which comprises contacting said susceptible tumor cells with the compound 2-((6-chrysenylmethyl)amino-2-methyl-1,3-propanediol or a pharmaceutically acceptable salt thereof.

6. The method of reducing the number of cells of a susceptible tumor which comprises contacting said susceptible tumor cells with 2-((6-chrysenylmethyl)amino-2-methyl-1,3-propanediol methanesulphonate.

7. A pharmaceutical composition in a form for parenteral or oral use containing the compound 2-((6-chrysenylmethyl)amino-2-methyl-1,3-propanediol or a pharmaceutically acceptable salt thereof together with a pharmaceutically acceptable carrier therefor.

* * * * *